US00PP21167P2

(12) United States Plant Patent
NeSmith

(10) Patent No.: US PP21,167 P2
(45) Date of Patent: Jul. 20, 2010

(54) SOUTHERN HIGHBUSH BLUEBERRY PLANT NAMED 'SUZIBLUE'

(50) Latin Name: ***Vaccinium* sp.**
Varietal Denomination: Suziblue

(76) Inventor: D. Scott NeSmith, 2227 Old Lifsey Springs Rd., Molena, GA (US) 30258

( * ) Notice: Subject to any disclaimer, the term of this patent is extended or adjusted under 35 U.S.C. 154(b) by 0 days.

(21) Appl. No.: 12/381,064

(22) Filed: Mar. 9, 2009

(51) Int. Cl.
*A01H 5/00* (2006.01)

(52) U.S. Cl. ..... Plt./157
(58) Field of Classification Search ..... Plt./157
See application file for complete search history.

*Primary Examiner*—Annette H Para
(74) *Attorney, Agent, or Firm*—Davis Wright Tremaine LLP

(57) ABSTRACT

The new variety 'Suziblue' is provided. The new and distinct variety ripens around the first week of May in southern Georgia. The fruit of the new variety 'Suziblue' are generally large, firm, and have good flavor. The new variety 'Suziblue' is vigorous with an estimated chilling requirement of about 400 hours at or below approximately 45° F. The asexually reproduced variety is reliably propagated vegetatively.

3 Drawing Sheets

STATEMENT REGARDING FEDERALLY-SPONSORED RESEARCH

This invention was made with U.S. Government support on behalf of U.S. Department of Agriculture, Hatch Act Grant No. GEO 01663. The U.S. Government has certain rights in this invention.

Latin name of the genus and species of the plant claimed: 'Suziblue' is a southern highbush blueberry plant that is a *Vaccinium* sp. hybrid.

Variety denomination: The new southern highbush blueberry plant claimed is of the variety denominated 'Suziblue'.

BACKGROUND OF THE INVENTION

The present invention relates to the discovery of a new and distinct cultivar of southern highbush blueberry plant botanically known as a *Vaccinium* sp. hybrid and herein referred to as 'Suziblue', as herein described and illustrated.

The new blueberry plant variety 'Suziblue' was selected in Griffin, Ga. in 2002. The new variety 'Suziblue' ripens around the first week of May in southern Georgia. The fruit of the new variety 'Suziblue' are generally large and have good flavor. The new variety 'Suziblue' is vigorous with an estimated chilling requirement of about 400 hours at or below approximately 45° F.

Pedigree and history: The new blueberry plant variety 'Suziblue' was selected in 2002 in Griffin, Ga. and originated from a cross of the female parent 'Star' (the subject of U.S. Plant Pat. No. 10,675) with the pollen parent 'TH-474' (unpatented). The pedigree of the new blueberry plant variety 'Suziblue' is complex and involves multiple *Vaccinium* species, including *V. corymbosum, V. darrowi*, and *V. ashei*. The pollen parent 'TH-474' was produced by a cross between 'TH-268' (unpatented) and 'MS-76' (unpatented). 'TH-268' was produced by a cross between 'Sharpblue' (unpatented) and 'US-67' (unpatented), and 'US-67' was produced by a cross between 'FL 9-A' (an unpatented *Vaccinium darrowi* species) and 'G-101' (unpatented). 'MS-76' was produced by a cross between 'G-180' (unpatented) and 'US-75' (unpatented), and 'US-75' was produced by a cross between 'FL 4-B' (an unpatented *Vaccinium darrowi* species) and 'Bluecrop' (unpatented). The new blueberry plant variety 'Suziblue' has been tested since 2003.

The new blueberry plant variety 'Suziblue' has been shown to maintain its distinguishing characteristics through successive asexual propagations by, for example, softwood cuttings. Plants from softwood cuttings have been directly planted in the ground.

SUMMARY OF THE INVENTION

The new blueberry plant variety 'Suziblue' has not been observed under all possible environmental conditions. The phenotype may vary somewhat with variations in environment and cultural practices such as temperature and light intensity without, however, any variance in genotype.

The following traits have been repeatedly observed in Alapaha and Griffin Ga., and are determined to be the unique characteristics of the new blueberry plant variety 'Suziblue':

1. Large berry size;
2. Sweet flavor;
3. Excellent plant vigor;
4. Firm to very firm fruit The new variety 'Suziblue' can be compared to the southern highbush blueberry varieties 'Star' (the subject of U.S. Plant Pat. No. 10,675) and 'Rebel' (the subject of U.S. Plant Pat. No. 18,138) .

Comparison to 'Star' (the subject of U.S. Plant Pat. No. 10,675). The new variety 'Suziblue' is an early season southern highbush blueberry plant that flowers and ripens at about the same time as 'Star'. The new variety 'Suziblue' typically produces berries that are similar in appearance to those of 'Star', however, the berry size of the new variety 'Suziblue' is larger than that of 'Star'. In addition, the new variety 'Suziblue' has demonstrated better berry firmness and overall better cropping than 'Star'. 'Suziblue' plant vigor has been equal to or superior to 'Star'.

Comparison to 'Rebel' (the subject of U.S. Plant Pat. No. 18,138). The new variety 'Suziblue' flower and ripens about one week later than 'Rebel'. The new variety 'Suziblue' typically produces berries that are larger in size than those of 'Rebel' and have a flavor that is noticably sweeter than that of 'Rebel', which has a mild to bland flavor.

BRIEF DESCRIPTION OF THE FIGURES

The accompanying photographic illustration shows typical specimens in full color of the foliage and fruit of the new variety 'Suziblue'. The colors are as nearly true as is reasonably possible in a color representation of this type.

BOTANICAL DESCRIPTION

Figure 1:
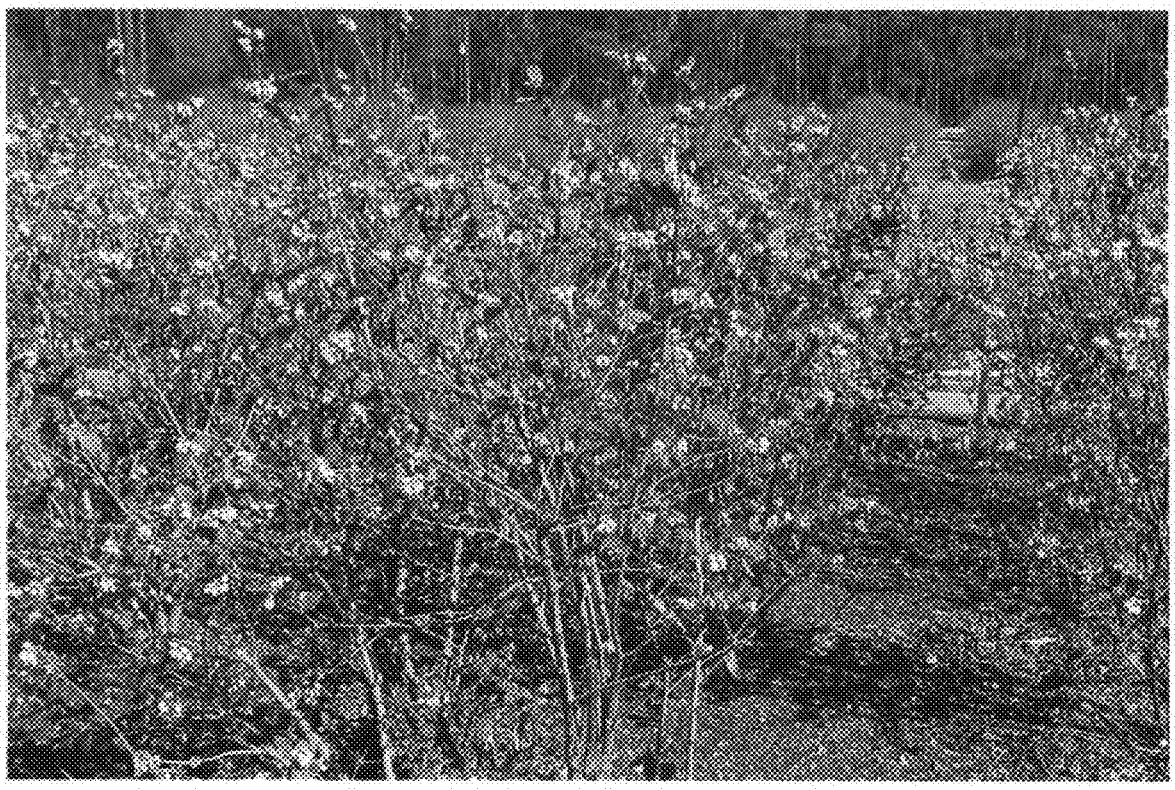
FIG. 1 is a photograph of the new variety 'Suziblue' during flowering as planted in a high density bark bed.
Figure 2:
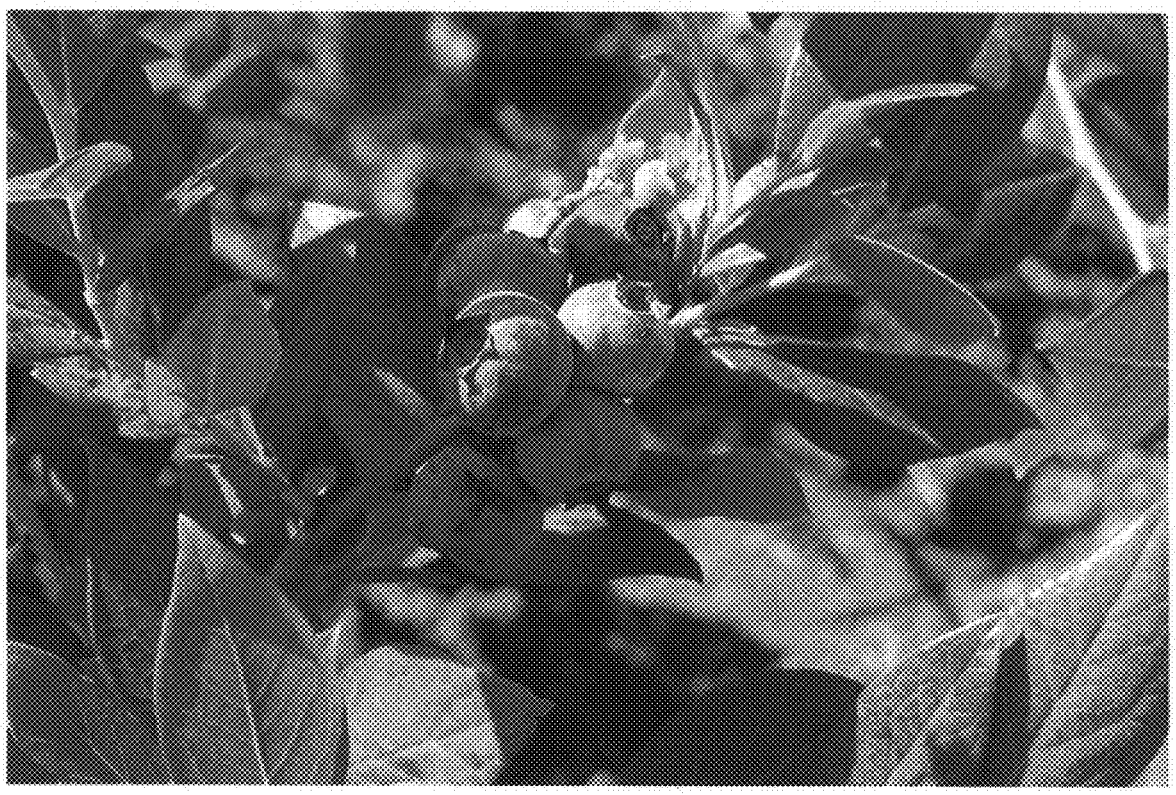
FIG. 2 is a photograph of the fruit of the new variety 'Suziblue' during ripening.
Figure 3:
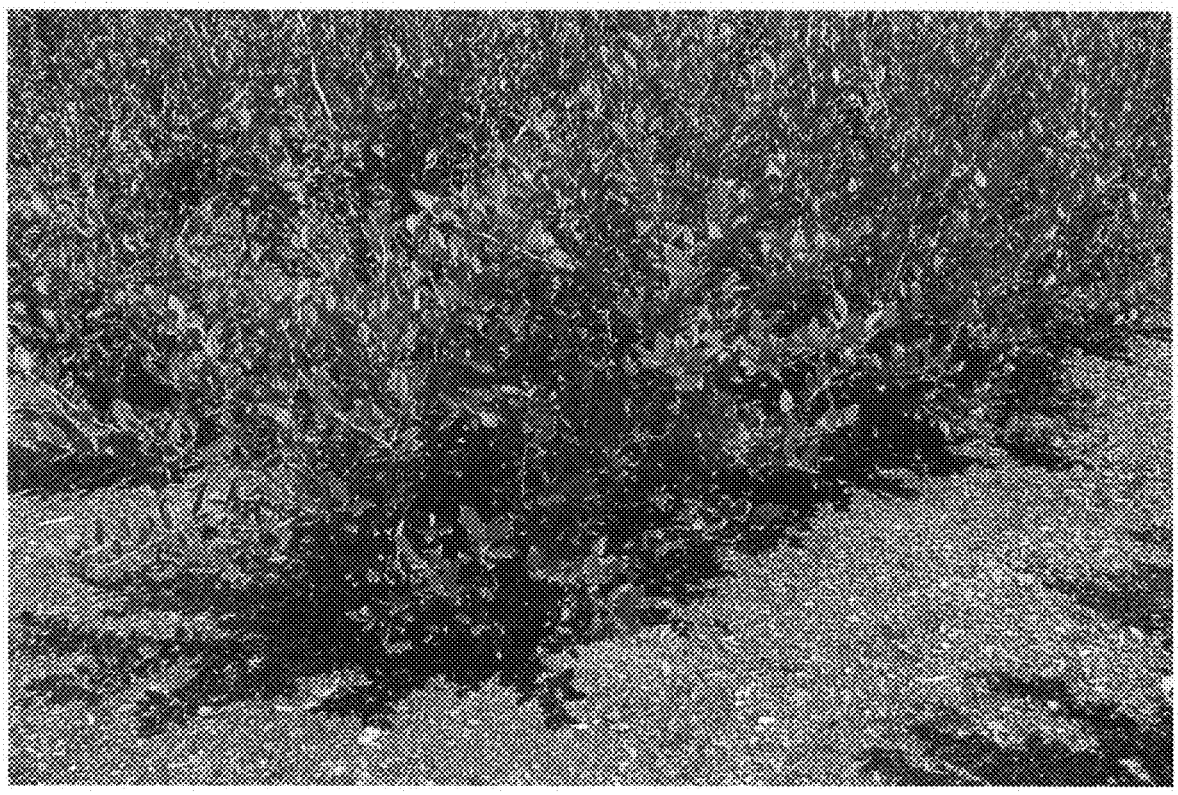
FIG. 3 is a photograph of the new variety 'Suziblue' during late summer of the second growing season as planted in a pine bark bed.

Throughout this specification, color names beginning with a small letter signify that the name of that color, as used in common speech, is aptly descriptive. Color names beginning with a capital letter designate values based upon the R.H.S. Colour Chart, $5^{th}$ edition published by The Royal Horticultural Society, London, England.

The following is a detailed description of the botanical and pomological characteristics of the new variety 'Suziblue'. Where dimensions, sizes, colors, and other characteristics are given, it is to be understood that such characteristics are approximations and averages set forth as accurately as practicable. The descriptions reported herein are largely from specimen plants grown in Alapaha and Griffin, Ga., with supplemental irrigation. Plants were about 3 to about 5 years old.

PLANT

Size: Approximately, 1.0 to 1.3 m tall by about 3 years of age.
Growth habit: Semi-spreading with approximately 2 to 5 canes arising from the crown.
Growth: Highly vigorous.
Productivity: High, averaging approximately 8 to 10 lbs per plant each year for 4 to 5 year old plants grown in bark beds with irrigation.
Hardiness: Similar to other southern highbush cultivars such as 'Star' (the subject of U.S. Plant Pat. No. 10,675) and 'Rebel' (the subject of U.S. Plant Pat. No. 18,138).
Chilling requirement: Approximately 400 hours of temperatures at or below about 45° F. (about 7° C.) to induce normal leafing and flowering during the spring.
Leafing: Plants readily break numerous leaf buds simultaneously with anthesis.
Canes:
*Diameter.*—Approximately 20 to 30 mm in plants that are about 3 years old and older. Approximately 8 to 12 mm in about 2 year old wood.
*Color.*—About Grey-Brown RHS 199D in plants that are about 3 years old and older. About Yellow-Green RHS 146D transitioning to about Brown RHS 200D in about 2 year old wood.

FOLIAGE

Leaf color: Healthy mature leaves
*Top side.*—About Green RHS 137B.
*Under side.*—About Yellow-Green RHS 148D.
Leaf arrangement: Alternate, simple.
Leaf shape: Elliptic.
Leaf margins: Entire.
Leaf venation: Reticulate.
Leaf apices: Broadly acuminate to broadly acute.
Leaf bases: Acute.
Leaf dimensions:
*Length.*—Approximately 65 to 75 mm
*Width.*—Approximately 30 to 35 mm.
Petioles: Small
*Length.*—Approximately 3.0 to 4.0 mm.
*Width.*—Approximately L8 to 2.0 mm.
*Color.*—About Yellow-Green RHS 145C.

FLOWERS

Date of 50% anthesis: March 1 (3 year average) in southeast Georgia; March 16 (3 year average) in middle Georgia.
Flower shape: Urceolate.
Flower bud number: Medium to high.
Flowers per cluster: Approximately 5 to 9.
Flower fragrance: None.
Corolla:
*Color.*—About White RHS 155B (open flower).
*Length.*—Approximately 7.8 to 8.5 mm.
*Width.*—Approximately 5.3 to 5.8 mm.
*Aperture width.*—Approximately 2.3 to 2.8 mm.
Flower peduncle:
*Length.*—Approximately 11.5 to 13.0 mm.
*Color.*—About Yellow-Green RHS 145C.
Flower pedicle:
*Length.*—Approximately 2.5 to 3.0 mm.
*Color.*—About Yellow-Green RHS 145C.
Calyx (with sepals):
*Diameter.*—Approximately 7.0 to 8.0 mm.
*Color (sepals).*—About Yellow-Green RHS 144D.
*Color (center of calyx).*—About Yellow-Green RHS 144A.
Stamen:
*Length.*—Approximately 6.3 to 6.7 mm.
*Number per flower.*—Approximately 10.
*Filament color.*—About Yellow-Green RHS 145C.
Style:
*Length.*—Approximately 7.0 to 8.0 mm.
*Color.*—About Yellow-Green RHS 145B.
Pistil:
*Length.*—Approximately 9.5 to 10.5 mm.
*Ovary color (exterior).*—About Yellow-Green RHS 144A.
Anther:
*Length.*—Approximately 4.0. to 4.5 mm.
*Number.*—Approximately 10.
*Color.*—About Greyed-Orange RHS 165B.
Pollen:
*Abundance.*—High.
*Color.*—About Yellow-Orange RHS 20B.
Self-compatibility: The cultivar has demonstrated a high degree of self-compatibility.

FRUIT

Date of 50% maturity: May 9 (3 year average) in southeast Georgia; May 19 (3 year average) in middle Georgia.
Fruit development period: Approximately 64 to 68 days.
Berry color:
*With wax.*—About Violet-Blue RHS 97C.
*With wax removed.*—About Greyed-Purple RHS 187A to about Black RHS 202A.

Berry surface wax abundance: Medium.

Berry flesh color: About Yellow-Green RHS 146D.

Berry weight:

*First harvest.*—Approximately 2.7 g to 3.1 g.

*Second harvest.*—Approximately 2.2 g to 2.6 g.

Berry size:

*Height from calyx to scar.*—Approximately 15.0 to 17.0 mm.

*Diameter.*—Approximately 18.0 to 22.0 mm.

Berry shape: Semi-spherical.

Fruit stem scar: Small, dry, no tearing.

Berry firmness: Firm to Very Firm.

Berry flavor and texture: Mild sweet flavor; firm, crisp texture.

Storage quality: Very good.

Suitability for mechanical harvesting: Slight.

Uses: Primarily used as fresh fruit for shipping.

SEED

Seed abundance in fruit: Low to medium.

Seed color: About Greyed-Orange RHS 165B.

Seed dry weight: Approximately 38.8 mg per 100.

Seed size: Approximately 1.5 to 2.4 mm long for fully developed seeds.

Typical plants of the new variety 'Suziblue' and two southern highbush varieties ('Star' and 'Rebel') were compared over a three-year period (2005–2008) at Alapaha, Ga. and tested for certain properties. Plants were established in 2002–2003. A severe freeze in 2007 prevented evaluations for that year. Rating scales are based on a 1 to 10 score, with 1 being the least desirable and 10 being the most desirable. Plant vigor is a relative scale (1 to 10) that considers overall robustness and durability of the plant itself (wood and vegetation). Plant vigor does not reflect berry quality, nor is it necessarily related to yield, especially annual yield. Values represent mean values ±the standard error with n=3. The approximate averages of these properties are as follows:

TABLE 1

COMPARISON OF THE NEW VARIETY 'SUZIBLUE' WITH OTHER BLUEBERRY PLANT VARIETIES AT ALAPAHA, GEORGIA

| Berry and plant attribute | 'Suziblue' | 'Star' | 'Rebel' |
|---|---|---|---|
| Berry size | 8.5 ± 0.1 | 8.5 ± 0.3 | 8.0 ± 0.2 |
| Berry scar | 8.0 ± 0.3 | 8.0 ± 0.3 | 8.5 ± 0.3 |
| Berry color | 8.0 ± 0.5 | 7.5 ± 0.3 | 7.7 ± 0.2 |
| Berry firmness | 8.0 ± 0.3 | 7.3 ± 0.2 | 8.0 ± 0.3 |
| Berry Flavor | 7.8 ± 0.3 | 7.2 ± 0.2 | 6.8 ± 0.1 |
| Crop load | 6.7 ± 1.1 | 5.3 ± 1.3 | 7.3 ± 1.2 |
| Plant vigor | 9.0 ± 0.3 | 8.5 ± 0.3 | 8.8 ± 0.4 |
| Date of 50% flowering | Mar. 1 ± 2.3 | Mar. 1 ± 4.6 | Feb. 23 ± 4.0 |
| Date of 50% ripening | May 9 ± 3.0 | May 8 ± 3.3 | May 2 ± 4.0 |

Yields of the new variety 'Suziblue' and two southern highbush varieties ('Star' and 'Rebel') were compared over a three-year period (2005–2008) for plants grown in a high density pine bark bed growing system at Alapaha, Ga. The plants were established in 2002–2003. A severe freeze in 2007 prevented evaluations for that year. Values are means ± the standard error with n=3 from single plant replications. The approximate values are as follows:

TABLE 2

COMPARISON OF YIELDS FOR THE NEW VARIETY 'SUZIBLUE' WITH OTHER BLUEBERRY PLANT VARIETIES AT ALAPAHA, GEORGIA

| | Cultivar yields (kg/plant) [Y] | | |
|---|---|---|---|
| Year | 'Suziblue' | 'Star' | 'Rebel' |
| 2005 | 0.54 ± 0.05 | 0.22 ± 0.07 | 0.44 ± 0.02 |
| 2006 | 5.14 ± 0.53 | 2.81 ± 0.11 | 4.10 ± 0.38 |
| 2008 | 5.41 ± 1.02 | 6.32 ± 0.85 | 4.20 ± 0.20 |

Typical plants of the new variety 'Suziblue' and the southern highbush standard cultivar 'Star' were compared over a three-year period (2005–2008) at Griffin, Ga. and tested for certain properties. Plants were established in 2003. A severe freeze in 2007 prevented evaluations for that year. Rating scales are based on a 1 to 10 score, with 1 being the least desirable and 10 being the most desirable. Plant vigor is a relative scale (1. to 10) that considers overall robustness and durability of the plant itself (wood and vegetation). Plant vigor does not reflect berry quality, nor is it necessarily related to yield, especially annual yield. Values represent mean values ± the standard error with n=3. The approximate averages of these properties are as follows:

TABLE 3

COMPARISON OF THE NEW VARIETY 'SUZIBLUE' WITH 'STAR' AT GRIFFIN, GEORGIA

| | Cultivar | |
|---|---|---|
| Berry and plant attributes [Y] | 'Suziblue' | 'Star' |
| Berry size | 8.7 ± 0.1 | 8.1 ± 0.1 |
| Berry scar | 8.1 ± 0.2 | 7.7 ± 0.2 |
| Berry color | 7.9 ± 0.3 | 7.3 ± 0.1 |
| Berry firmness | 8.0 ± 0.2 | 7.1 ± 0.1 |
| Berry flavor | 7.8 ± 0.2 | 7.2 ± 0.1 |
| Cropping | 5.8 ± 1.1 | 4.0 ± 1.3 |
| Plant vigor [Z] | 7.8 ± 0.2 | 7.9 ± 0.1 |
| Date of 50% flowering | Mar. 16 ± 1.2 | March 16 ± 3.2 |
| Date of 50% ripening | May 19 ± 3.2 | May 19 ± 3.8 |

Average berry weight and berry firmness of the new variety 'Suziblue' and the southern highbush standard cultivar 'Star' were compared using a FirmTech 2 firmness tester for plants grown at Griffin, Ga. Data were taken in 2006 and 2008. A severe freeze during 2007 prevented evaluations. Values are means ± the standard error with n=3 from single plant replications. The approximate values are as follows:

TABLE 4

COMPARISON OF AVERAGE BERRY WEIGHT AND BERRY FIRMNESS FOR THE NEW VARIETY 'SUZIBLUE' WITH WITH 'STAR' AT GRIFFIN, GEORGIA

| | Average berry wt (g) | | Berry firmness (g/mm) | |
|---|---|---|---|---|
| Year | 'Suziblue' | 'Star' | 'Suziblue' | 'Star' |
| 2006 | 2.19 ± 0.10 | 1.46 ± 0.10 | 216 ± 4.3 | 182 ± 4.6 |
| 2008 | 2.78 ± 0.12 | 2.22 ± 0.15 | 207 ± 2.6 | 209 ± 4.0 |

Typical plants of the new variety 'Suziblue' and two southern highbush varieties ('Star' and 'Rebel') were compared and tested for certain properties in 2008 on farm test plots at 4 locations in south Georgia within Appling, Bacon and Ware counties. Plants were established at the test sites in 2007. Rating scales are based on a 1 to 10 score, with 1 being the least desirable and 10 being the most desirable. Plant vigor is a relative scale (1 to 10) that considers overall robustness and durability of the plant itself (wood and vegetation). Plant vigor does not reflect berry quality, nor is it necessarily related to yield, especially annual yield. Values represent mean values ±the standard error with n=4. The approximate averages of these properties are as follows:

TABLE 5

COMPARISON OF THE NEW VARIETY 'SUZIBLUE' WITH OTHER BLUEBERRY PLANT VARIETIES IN SOUTHERN GEORGIA

| | Cultivar | | |
|---|---|---|---|
| Berry and plant attributes | 'Suziblue' | 'Star' | 'Rebel' |
| Berry size | 8.7 ± 0.1 | 8.2 ± 0.1 | 8.5 ± 0.1 |
| Berry scar | 8.3 ± 0.1 | 7.3 ± 0.1 | 8.3 ± 0.3 |
| Berry color | 7.5 ± 0.2 | 7.4 ± 0.1 | 7.5 ± 0.2 |
| Berry firmness | 7.9 ± 0.2 | 7.4 ± 0.1 | 8.3 ± 0.1 |

TABLE 5-continued

COMPARISON OF THE NEW VARIETY 'SUZIBLUE' WITH OTHER BLUEBERRY PLANT VARIETIES IN SOUTHERN GEORGIA

| | Cultivar | | |
|---|---|---|---|
| Berry and plant attributes | 'Suziblue' | 'Star' | 'Rebel' |
| Berry flavor | 7.7 ± 0.1 | 7.3 ± 0.1 | 6.8 ± 0.1 |
| Cropping | 7.3 ± 0.6 | 5.0 ± 1.2 | 5.5 ± 1.0 |
| Plant vigor | 9.1 ± 0.4 | 8.0 ± 0.4 | 8.3 ± 0.4 |
| Date of 50% flowering | Mar. 3 ± 4.5 | Mar. 2 ± 3.8 | Feb. 23 ± 3.8 |
| Date of 50% ripening | May 9 ± 1.7 | May 7 ± 1.5 | May 1 ± 1.5 |

What is claimed is:

1. A new and distinct variety of southern highbush blueberry plant named 'Suziblue', substantially as illustrated and described herein.

* * * * *